US007544711B2

(12) United States Patent
Del Soldato et al.

(10) Patent No.: US 7,544,711 B2
(45) Date of Patent: Jun. 9, 2009

(54) USE OF NITRODERIVATIVES IN URINARY INCONTINENCE

(75) Inventors: Piero Del Soldato, Milan (IT); Francesco Sannicolo', Milan (IT)

(73) Assignee: Nicox S.A., Sophia Antipolis (FR)

( * ) Notice: Subject to any disclaimer, the term of this patent is extended or adjusted under 35 U.S.C. 154(b) by 125 days.

(21) Appl. No.: 11/018,501

(22) Filed: Dec. 22, 2004

(65) Prior Publication Data
US 2005/0101661 A1    May 12, 2005

Related U.S. Application Data

(62) Division of application No. 09/147,770, filed as application No. PCT/EP97/04774 on Sep. 2, 1997, now abandoned.

(30) Foreign Application Priority Data
Sep. 4, 1996    (IT)    .............................. MI96A1821

(51) Int. Cl.
A01N 43/16    (2006.01)
A01N 37/00    (2006.01)
A61K 31/21    (2006.01)
C07D 311/00   (2006.01)
C07C 203/00   (2006.01)
C07C 331/00   (2006.01)
C07C 381/00   (2006.01)

(52) U.S. Cl. ...................... 514/456; 514/509; 549/401; 558/482

(58) Field of Classification Search ................. 514/456, 514/509; 549/401; 558/482
See application file for complete search history.

(56) References Cited

U.S. PATENT DOCUMENTS

| 2,809,194 A | 10/1957 | Novello et al. ................. 544/12 |
| 2,937,169 A | 5/1960 | Hinkley ........................ 544/12 |
| 2,976,289 A | 3/1961 | Cohen et al. ................. 544/285 |
| 3,043,840 A | 7/1962 | Downing, Jr. ................. 544/13 |
| 3,055,904 A | 9/1962 | Graf et al. .................... 546/200 |
| 3,058,882 A | 10/1962 | Stürm et al. ................. 514/155 |
| 3,161,654 A | 12/1964 | Shen .......................... 260/319 |
| 3,255,241 A | 6/1966 | Schultz et al. ............... 562/431 |
| 3,313,848 A | 4/1967 | Scherrer et al. ............. 562/454 |
| 3,360,518 A | 12/1967 | Shetty ........................ 544/288 |
| 3,392,168 A | 7/1968 | Lund et al. .................... 544/13 |
| 3,415,834 A | 12/1968 | Hoffmann et al. ........... 546/310 |
| 3,565,911 A | 2/1971 | Beregi et al. ................. 548/483 |
| 3,600,437 A | 8/1971 | Marshall ...................... 73/71.5 |
| 3,665,002 A | 5/1972 | Popelak et al. .............. 548/252 |
| 3,758,506 A | 9/1973 | Godfroid et al. ............. 547/379 |
| 3,784,701 A | 1/1974 | Tomcufcik et al. .......... 424/317 |
| 3,787,440 A | 1/1974 | Hamano et al. ........... 260/326.1 |
| 3,806,534 A | 4/1974 | Feit et al. .................... 558/399 |
| 3,840,597 A | 10/1974 | Moore et al. ................. 564/97 |
| 3,843,681 A | 10/1974 | Demerson et al. ............... 53/76 |
| 3,997,669 A | 12/1976 | Carney et al. ................ 424/274 |
| 4,018,929 A | 4/1977 | Delarge et al. .............. 514/355 |
| 4,035,376 A | 7/1977 | Janssen et al. .............. 260/295 |
| 4,954,518 A | 9/1990 | Takano et al. ................ 514/456 |
| 5,859,053 A | 1/1999 | Lesur et al. |
| 5,861,426 A | 1/1999 | Del Soldato et al. |
| 6,040,341 A | 3/2000 | Del Soldato et al. |

FOREIGN PATENT DOCUMENTS

| BE | 605302 | 7/1961 |
| DE | 1149015 | 5/1963 |
| DE | 1163332 | 2/1964 |
| DE | 3834204 | 4/1989 |
| EP | 0 738 706 A1 | 10/1996 |
| EP | 0 722 434 B1 | 7/1998 |

(Continued)

OTHER PUBLICATIONS

Wallace, J. L., et al. Gastroenterology 1994, 107, 173-179.*
Ward, A., et al. Drugs 1988, 36, 732-753.*
Morrison, Robert Thornton, and Robert Neilson Boyd. Organic Chemistry. Boston:Allyn, 1973. pp. 591 and 603.*
Savage (Medsafe, 2002), p. 1-3.*
Yoshikawa et al. (JP 06206859)—Abstract (p. 1-4).*

(Continued)

*Primary Examiner*—Sreeni Padmanabhan
*Assistant Examiner*—Umamaheswari Ramachandran
(74) *Attorney, Agent, or Firm*—Arent Fox LLP

(57) ABSTRACT

The present invention relates to the use of the following compounds, their compositions, and their salts for the preparation of medicaments for the treatment of urinary incontinence and other diseases, the compounds having the general formula:

$$A\text{-}X_1\text{—}NO_2$$

wherein:
A=RCO(X)$_t$, wherein t is the integer 0 or 1;
X=O, NH, NR$_{1C}$, wherein R$_{1C}$ is a linear or branched C$_1$ to C$_{10}$ alkyl group;
when t=1, R= 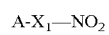

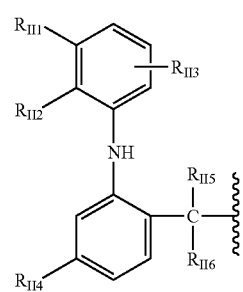

and X$_1$=—YO—, wherein Y is a C$_1$ to C$_{20}$ alkylene, C$_5$ to C$_7$ cycloalkyl or oxyalkyl derivative.

4 Claims, No Drawings

FOREIGN PATENT DOCUMENTS

| | | |
|---|---|---|
| FR | 1574570 | 7/1969 |
| GB | 1195628 | 6/1970 |
| JP | 73 05 585 | 2/1973 |
| WO | 94/04484 | 3/1994 |
| WO | 94/12463 | 6/1994 |
| WO | 94/13635 | 6/1994 |
| WO | 95/15315 | 6/1995 |
| WO | 95/30641 | 11/1995 |
| WO | WO 95/30641 * | 11/1995 |
| WO | 96/23786 | 8/1996 |
| WO | 97/16405 | 5/1997 |
| WO | WO 98/09948 A2 | 3/1998 |
| WO | WO 98/09948 A3 | 3/1998 |
| WO | WO 00/51988 A1 | 9/2000 |
| WO | WO 00/61537 A2 | 10/2000 |
| WO | WO 00/61537 A3 | 10/2000 |
| WO | WO 01/12584 A2 | 2/2001 |
| WO | WO 01/12584 A3 | 2/2001 |

OTHER PUBLICATIONS

Ferguson et al., "Urinary Bladder Function and Drug Development", *Trends Pharmacol. Sci.* 17, 161-165, 1996.

Anderson, "Pharmacology of Lower Urinary Tract Smooth Muscle, and Penile Erectile Tissues", *Pharmacol. Rev.* 45, 253-308, 1993.

Rice, "Topical Spinal Administration of Nitric Oxide Synthase Inibitor Prevents the Hyper-Reflexia Associated with a Rat Model of Persistent Visceral Pain", *Neurosci. Lett.* 187, 111-114, 1995.

Wilkinson, *J. Chem. Soc.* 32, 1948.

Winter et al., "Carrageenin-Induced Edema in Hind Paw of the Rat as an Assay for Antiinflammatory Drugs", *Proc. Soc. Exp. Biol. Med.* 111, 544-547, 1962.

Fahry-Rd et al., *CIRC-RES.* 72/6 (12020-1210) 1983.

Izumi et al., "Gestational Changes in L-arginine-induced relaxation of Pregnant Rat and Nonpregnant Myometrial Contractility", *Am. J. Obstet Gynencol.* 169, 1327-1337, 1983.

Merck Index, 10$^{th}$ Edition, Windhoz et al. "Merck & Co.", Rahway, N.J.

Morikawa et al., 110CA: 85899.

Persson et al., 117CA:445429, 1992.

Chung et al., 125CA:105692, 1996.

European Search Report dated Aug. 6, 2004.

Close et al., "Synthesis of Potential Diuretic Agents. I. Derivatives of 7-Sulfamyl-3,4-dihydro-1,2,4-benzothiadiazine 1,1-Dioxide", *J. Am. Chem. Soc.* 82, 1132, 1960.

Del Soldato et al., "The anesthetized Guinea Pig as a Versatile Pharmacological Test Object", *J. Pharmacol. Meth.* 5, 278-285, 1981.

Janes et al. "Flow Cytometric Detection of Circulating Activated Platelets and Platelet hyperresponsiveness in Pre-Eclampsia and Pregnancy", *Clin. Sci.* 86, 731-739, 1994.

Dubois et al., "increased Cyclooxigenase-2 Levels in Carcinogen-Induced Rat Colonic Tumors", *Gastroenterol.* 110, 1259-1262, 1996.

Zhou et al., The Inhibitory Mechanism of Nicorandil in Isolated Rat Urinary Bladder and Femoral Atrery, *Eur. J. Pharmacol.*, 59, 153-159, 1995.

Howe et al., "ZENECA ZD 6169: A Novel $K_{ATP}$ Channel Opener with in Vivo Selectivity for Urinary Bladder", *J. Pharmacol. Exp. Ther.* 274, 884-890, 1995.

Maggi et al., "Prostanoid Modulate Reflex Micturition by Acting Through Capsaicin-Sensitive Afferents", *Eur. J. Pharmacol.*, 105-112, 1988.

Malmgren et al., "Custometrical Evaluation of Bladder Instability in Rats with Intraversical Obstruction", *J. Urol.* 137, 1291-1294, 1987.

Werkström et al., "Factors Involved in the Relaxation of Female Pig Urethra Evoked by Electrical Field Stimulation" *Br. J. Pharmacol.* 116, 1599-1604, 1995.

Assreuy et al., "Feedback Inhibition of Nitric Oxide Synthase Activity by Nitric Oxide", *Br. J. Pharmacol.*, 833-837, 1993.

O.A. al-Swayeh et al.; "Nitroparacetamol exhibits anti-inflammatory and anti-nociceptive activity"; British Journal of Pharmacology; 2000; 130; pp. 1453-1456; Macmillan Publishers Ltd.

Adrian W. Bak et al.; "Cyclooxygenase-Independent Chemoprevention With An Aspirin Derivative In a Rat Model of Colonic Adenocarcinoma"; Life Sciences; vol. 62; No. 23; 1998; pp. 367-373; Elsevier Science Inc.

Viviane Bertrand et al.; Role of tumour necrosis factor-a and inducible nitric oxide synthase in the prevention of nitro-flurbiprofen small intestine toxicity; European Journal of Pharmacology 356; 1998; pp. 245-253; Elsevier Science B.V.

Richard J. Bing et al.; "The Pharmacology of a New Nitric Oxide Donor: B-NOD"; Biochemical and Biophysical Research Communications 275; 2000; pp. 350-353; Academic Press.

Gary L. Wenk et al.; Mechanisms to prevent the toxicity of chronic neuroinflammation on forebrain cholinergic neurons; European Journal of Pharmacology 402; 2000; pp. 77-85; Elsevier Science B.V.

* cited by examiner

USE OF NITRODERIVATIVES IN URINARY INCONTINENCE

This is a divisional of U.S. patent application Ser. No. 09/147,770, filed on Apr. 28, 1999 now abandoned, which is the U.S. national phase of PCT/EP97/04774, filed on Sep. 2, 1997, the contents of both applications are hereby incorporated by reference herein in their entirety.

The present invention relates to new medicaments to be used in urinary disorders. These disorders are generally grouped in one single functional pathology class and are characterized by several symptoms, including changes in micturition (like for example incontinence), changes in urinary output (like for example polyuria, oliguria, anuria), changes in the appearance of urine (like for example hematuria), edema (like for example anasarca), pain (like for example bladder pain).

The invention relates to new compounds having superior efficacy in the treatment of some forms of urinary incontinence (anti-incontinence compounds) or edema (diuretics) and which appear to be well tolerated by the body.

In particular, it is known that urinary incontinence can be considered a disorder of micturition control resulting from a lesion or dysfunction of the lower urinary tract. In particular, the urinary bladder smooth muscle called detrusor muscle and the internal (smooth muscle) and external (striated muscle) urethral sphincters are involved. See for example Ferguson D. and Christopher N., *Urinary bladder function and drug development*, Trends in Pharmacological Sciences, 1996, 17, 161-165. This publication reports that there are various types of incontinence characterised by different causes and symptoms. In particular, the following can be mentioned:

stress incontinence, which is the discharge of small amounts of urine due to increased intraabdominal pressure caused, for example, by cough or an effort. Stress incontinence is due to a change in vesicourethral angle and relaxation of the urethral sphincter muscle. Stress incontinence is frequent in women, particular multipara women.

urge incontinence, which is the inability to control the urinary bladder and manifests itself with a sudden and urgent stimulus to urinate. Urge incontinence is due to intermittent contraction of the urinary bladder muscle for no apparent cause (detrusor instability) or caused by interstitial cystitis or other inflammatory phenomena which lead to urinary bladder hyperexcitability. It seems that changes in urinary bladder innervation are present in all these cases;

incontinence from urinary bladder overdistention, which occurs in case of chronic urinary retention due to obstructive causes. The urinary bladder never empties completely, resulting in continous discharge of small amounts of urine.

total incontinence, which is a complete lack of urinary bladder control due to inability of controlling the sphincters. It is the result of severe neurologic damages.

In the known art, the available therapies are based on three different approaches, see for example the above publication and Anderson K. E. , *Pharmacology of lower urinary tract smooth muscles and penile erectile tissues*, Pharmacological Reviews, 1993, 45, 253-308:

reduced detrusor activity, changed sensory nervous transmission, changed urethral resistance.

According to the first approach, detrusor contraction is stimulated by the parasympathetic system and acetylcholine is the main mediator. Therefore, anticholinergic agents are used to reduce vesical hyperactivity. However, these are effective but of limited use due to the systemic anticholinergic side effects including for example dry mouth, constipation and tachycardia. Taking into account that vesical irritability is often associated with urinary bladder obstructive disease, the administration of anticholinergic agents risks triggering an acute urinary retention crisis.

Another pharmacological approach to reduce detrusor activity includes the use of medicaments which help opening potassium channels or calcium antagonists which relax the smooth muscle. However, there are disadvantages such as a marked hypotensive action due to a nonspecific vasodilator effect produced by these agents.

An additional pharmacological measure to reduce detrusor activity consists of the use of prostaglandin synthesis inhibitors which were tested in some detrusor hyperactivity and enuresis cases with promising results but giving major side effects. Their use is based on the fact that numerous prostaglandins were found to be synthesised in the urinary bladder following nervous stimulation and some of them seem to act as mediators of detrusor contraction. Additionally, some prostaglandines may be involved in severe urge incontinence and vesical hyperactivity events during some inflammatory disease of the urinary tract.

Therefore, nonsteroidal anti-inflammatory drugs are potentially useful in lowering the urinary bladder excitability threshold, and are thus effective in cases of detrusor instability. Unfortunately, they have the disadvantage of being little tolerated at active doses, especially in the gastrointestinal tract.

Likewise, NO synthetase enzyme inhibitors can prevent hyperexcitability of the urinary bladder and hyperalgesia resulting from inflammatory events such as interstitial cystitis; see Rice A. S. C., *Topical spinal administration of a nitric oxide synthase inhibitor prevents the hyperreflexia associated with a rat model of persistent visceral pain*, Neuroscience Letters, 1995, 187, 111-114. However, there are currently no agents of this type which can be used therapeutically due to a relative nonspecificity of their pharmacological profile.

The second approach, which consists of changing sensory nervous transmission (whenever urinary incontinence results from lesions of the nervous system), includes the use of drugs which act on neurotransmission, for example gamma-aminobutyric acid (GABA), or peptides, or purines, which are important neurotransmitters in the urinary tract.

Studies are also known which use capsaicin for intravesical instillation with sometimes satisfactory results. However, this treatment has limited clinical applications due to its transient effect, which, in addition, can be obtained only by local use.

The third approach considers the fact that muscle tone in the urethra is mediated by different neurotransmission systems, including for example the adrenergic system, by stimulation of α-receptors, α-agonist medicaments, which increase the pressure borne by the urethra, are used to change urethral resistance sometimes with satisfactory results. However, the use of these compounds involves some risks, as in the case of urinary bladder obstructive disease where even alpha-antagonists are used. In these cases a sphincter hyperactivity is observed, which prevents regular urinary bladder voiding causing urge incontinence. Also in this case, as in the first approach described above, severe side effects of a hypontensive type related to the α-antagonistic activity in the cardiocirculatory system are observed.

To increase urethral resistance in women with stress incontinence, an oestrogen based therapy which was found to be efficacious in increasing intraurethral pressure and in changing the structure of mucous membrane, vessel and connective, is used. Good results were observed combining treatment with α-agonists with oestrogen treatment. However, the well known side effects which occur when oestrogen treatment is used must be reported.

So far, commercial pharmaceutical preparations resolve the problem only in a limited number of cases. However, they generally cause side effects, even somewhat severe.

The Applicant has unexpectedly and surprisingly found that the particular classes of compounds described below can be beneficially used in the treatment of the various types of urinary incontinence described above, as they exhibit a pharmacological profile superior to that of the known preparations used for this type of disease.

An object of the present invention is the use for the treatment of urinary incontinence of the following classes of compounds, having the general formula:

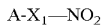

or their salts, wherein
$A=R(COX)_t$ where t is an integer 0 or 1;
$X=O$, NH, $NR_{1C}$ where $R_{1C}$ is a linear or branched alkyl having from 1 to 10 C atoms;
R is chosen from the following groups:
Group IA), wherein t=1

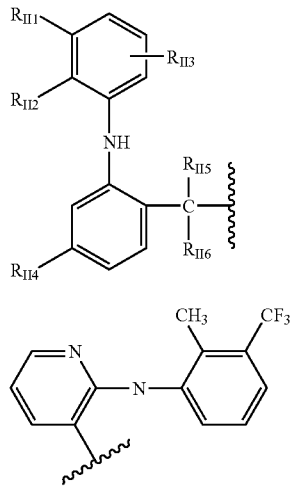

wherein
$R_{II5}$ is H, a linear or whenever possible branched $C_1$-$C_3$, alkyl;
$R_{II6}$ has the same meaning as $R_{II5}$, or when $R_{II5}$ is H it can be benzyl;
$R_{II1}$, $R_{II2}$ and $R_{II3}$ equal or different, are hydrogen, linear or whenever possible branched $C_1$-$C_6$ alkyl or $C_1$-$C_6$ alkoxy, or Cl, F, Br;
$R_{II4}$ is $R_{II1}$ or bromine;
preferred are the compounds where $R_{II1}$, $R_{II2}$ and $R_{II4}$ are H, and $R_{II3}$ is Cl, and $R_{II3}$ is in the ortho position to NH; $R_{II5}$ and $R_{II6}$ are H, X is equal to O, and $X_1$ is $(CH_2-CH_2-O)_2$;
(IAb) is the residue of 2-[[2-methyl-3-(trifluoro-methyl)phenyl]amino]-3-pyridinecarboxylic acid and when —COOH is present it is known as flunixin.

The compounds preferred are those where X=O;
IIA) chosen from the following
wherein when t=1,

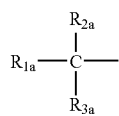

wherein
$R_{2a}$ and $R_{3a}$ are H, a linear or whenever possible branched substituted or non-substituted $C_1$-$C_{12}$ alkyl, allyl, with the proviso that when one of the two is allyl the other is H; preferably $R_{2a}$ is H, alkyl has from 1 to 4 C atoms, $R_{3a}$ is H;
$R_{1a}$ is chosen from
II Aa)

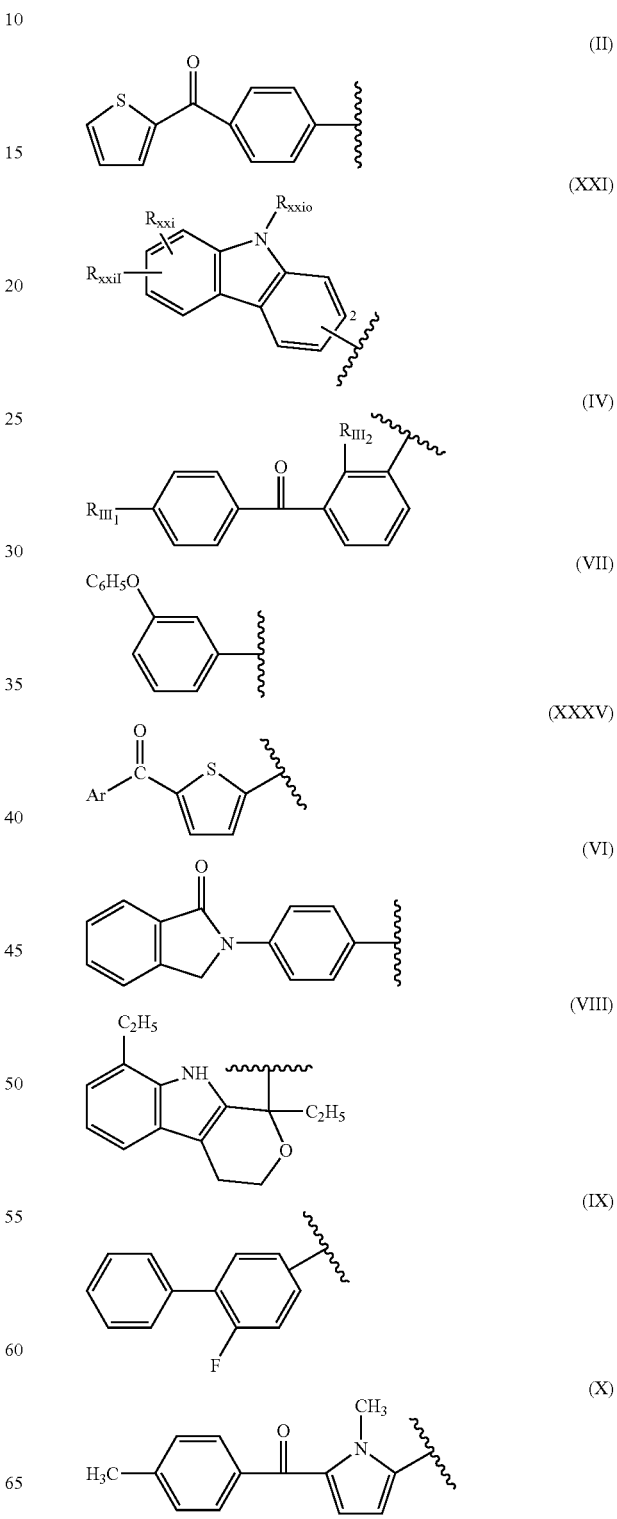

-continued

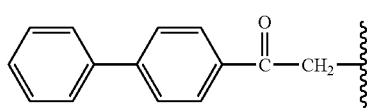
(III)

wherein
in the compounds of formula (IV), residue of ketoprofen:
$R_{III1}$ is H, $SR_{III3}$ where $R_{III3}$ contains from 1 to 4 C atoms linear or whenever possible branched;
$R_{III2}$ is H, hydroxy;
preferred are the compounds where $R_{III1}$ and $R_{III2}$ are H, $R_{3a}$ is H, and $R_{2a}$ is methyl, X=O;
in the compounds of formula (XXI), residue of carprofen:
$R_{xxio}$ is H, a linear or whenever possible branched alkyl having from 1 to 6 carbon atoms, a $C_1$-$C_6$ alkoxycarbonyl bound to a $C_1$-$C_6$ alkyl, a $C_1$-$C_6$ carboxyalkyl, a $C_1$-$C_6$ alkanoyl, optionally substituted with halogen, benzyl or halobenzyl, benzoyl or halobenzoyl;
$R_{xxi}$ is H, halogen, hydroxy, CN, a $C_1$-$C_6$ alkyl optionally containing OH groups, a $C_1$-$C_6$ alkoxy, acetyl, benzyloxy, $SR_{xxi2}$ where $R_{xxi2}$ is $C_1$-$C_6$ alkyl; a perfluoroalkyl having from 1 to 3 C atoms, a $C_1$-$C_6$ carboxyalkyl optionally containing OH, $NO_2$, sulphamoyl, dialkyl sulphamoyl groups with the alkyl having from 1 to 6 C atoms, or difluoroalkylsulphonyl with the alkyl having from 1 to 3 C atoms;
$R_{xxi1}$ is halogen, CN, a $C_1$-$C_6$ alkyl containing one or more OH, a $C_1$-$C_6$ alkoxy, acetyl, acetamide, benzyloxy groups, $SR_{III3}$ is as above defined, a perfluoroalkyl having from 1 to 3 C atoms, hydroxy, a carboxyalkyl having from 1 to 6 C atoms, $NO_2$, amino, a mono- or dialkylamino having from 1 to 6 C atoms, sulphamoyl, a dialkyl sulphamoyl having from 1 to 6 C atoms, or difluoroalkylsulphamoyl as above defined; or $R_{xxi}$ together with $R_{xxi1}$ is an alkylene dioxy having from 1 to 6 C atoms;
preferred are the compounds where $R_{xxio}$ is H, the connectiong bridge is at position 2, $R_{xxi}$ is H, $R_{xxi1}$ is chlorine and is in para position to nitrogen;
$R_{3a}$ is H, $R_{2a}$ is methyl and X is O;
in the compounds of formula (XXXV), residue of thiaprofenic acid:
Ar is phenyl, hydroxyphenyl optionally mono or polysubstituted with halogen, an alkanoyl or alkoxy having from 1 to 6 C atoms, a trialalkyl having from 1 to 6 C atoms, preferably from 1 to 3 C atoms, cyclopentyl o-hexyl o-heptyl, heteroaryl, preferably thienyl, furyl optionally containing OH, pyridyl;
the preferred compounds of formula (XXXV) are those where Ar is phenyl, $R_{3a}$ is H, $R_{2a}$ is methyl and X is O;
in the compounds of formula (II), residue of suprofen, of which the preferred, where $R_{3a}$=H, $R_{2a}$=$CH_3$ and X=O, has been shown, its equivalents, as described and obtained in patent U.S. Pat. No. 4,035,376, herein incorporated by reference, can be used.
in the compounds of formula (VI), of which the preferred, indoprofen, when $R_{2a}$ is $CH_3$ or indobufen, when $R_{2a}$ is equal to H and $R_{3a}$=$CH_3$ and X=O, have been shown, its equivalents, as described and obtained in accordance with patent U.S. Pat. No. 3,997,669, herein incorporated by reference, can be used.
in the compounds of formula (VIII), of which the preferred etodolac, when $R_{3a}$=$R_{2a}$=H and X=O, has been shown, its equivalents as described and obtained according to patent U.S. Pat. No. 3,843,681, herein incorporated by reference, can be used;
in the compounds of formula (VII), of which the preferred, fenoprofen, when $R_{3a}$=H, $R_{2a}$=$CH_3$ and X=O, has been shown, its equivalents, as described and obtained according to patent U.S. Pat No. 3,600,437, herein incorporated by reference, can be used;
in the compounds of formula (III), of which the preferred, fenbufen, when $R_{3a}$=$R_{2a}$=H and X=O, has been shown, its equivalents, as described and obtained according to patent U.S. Pat. No. 3,784,701, herein incorporated by reference, can be used;
in the compounds of formula (X), residue of tolmetin, when $R_{3a}$=$R_{2a}$=H and X=O, its equivalents, as described and obtained according to patent FR 1.574.570, herein incorporated by reference, can be used;
in the compounds of formula (IX), residue of flurbiprofen, when $R_{3a}$=H, $R_{2a}$=$CH_3$ and X=O, its equivalents as described in the known art can be used;

II Ab)

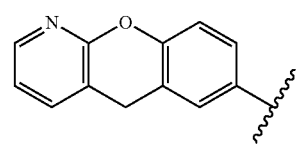
(IIIa)

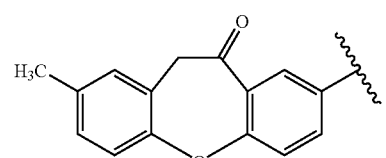
(XXX)

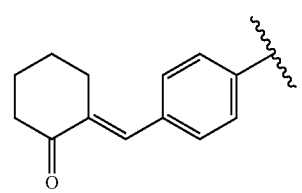
(XXXI)

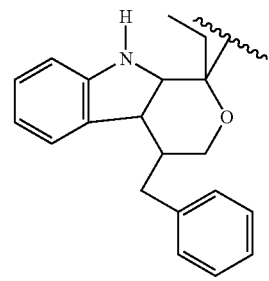
(XXXII)

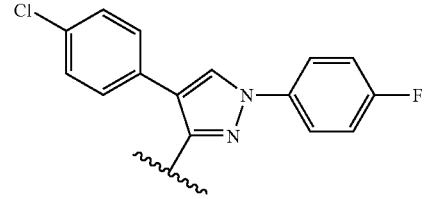
(XXXIII)

-continued (XXXVI)

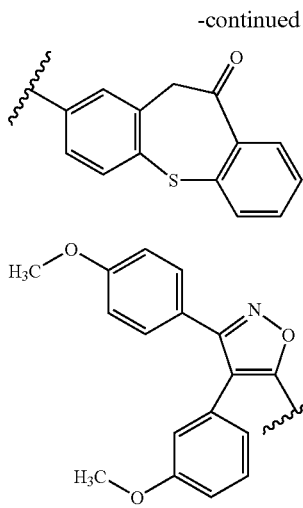

(XXXVII)

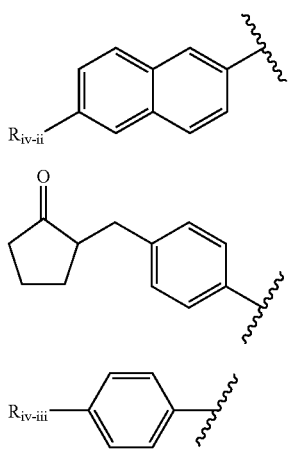

where the meanings are as follows:
when IIIa) contains —CH(CH₃)—COOH it is known as pranoprofen: α-methyl-5H-[1] benzopyran [2,3-b]pyridine-7-acetic acid. In the preferred compounds $R_{2a}$=H, $R_{3a}$=CH₃ and X=O;
when residue (XXX) contains —CH(CH₃)—COOH it is known as bermoprofen: dibenz [b,f] oxepin-2-acetic acid. The preferred compound is that with X=O, $R_{2a}$=H, $R_{3a}$=CH₃;
residue (XXXI) is known as CS-670, 2-[4(2-oxo-1-cyclohexylidenemethyl)phenyl]propionic acid, when the radical is —CH(CH₃)—COOH. The preferred compound has $R_{2a}$=H, $R_{3a}$=CH and X=O;
residue (XXXII) derives from the known pemedolac which contains group —CH₂COOH. The compound preferred has $R_{2a}$=$R_{3a}$=H and X=O;
when residue (XXXIII) is saturated with —CH₂COOH it is known as pyrazolac: 4-(4-chlorophenyl)-1-(4-fluorophenyl)3-pyrazolyl acid derivatives. The preferred compounds have $R_{2a}$=$R_{3a}$=H and X=O;
when residue (XXXVI) is saturated with —CH(CH₃)—COO— it is known as zaltoprofen. When the residue is saturated with a hydroxy or amine group or the acid salts, the compounds are known as dibenzothiepin derivatives. The compounds preferred have $R_{2a}$=H, $R_{3a}$=CH₃ and X=O;
when residue (XXXVII) is CH₂—COOH it derives from the known mofezolac: 3,4-di(p-methoxyphenyl)isoxazol-5-acetic acid. The preferred compounds include $R_{2a}$=$R_{3a}$=H, t=1, X=O.
Group III A), where t=1,

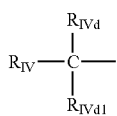

where
$R_{IVd}$ and $R_{IVd1}$ are at least one H and the other a linear or whenever possible branched C₁-C₆ alkyl, preferably C₁ and C₂, or difluoroalkyl with the alkyl having from 1 to 6 C atoms, preferred is C₁, or $R_{IVd}$ and $R_{IVd1}$ jointly form a methylene group;

$R_{IV}$ has the following meaning:

(II)

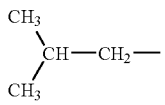

(X)

(III)

where the compounds of group III A) have the following meanings:
in the compounds of formula (II):
$R_{IV-II}$ is an alkyl having from 1 to 6 C atoms, a cycloalkyl having from 3 to 7 C atoms, an alcoxymethyl having from 1 to 7 C atoms, a trifluoroalkyl having from 1 to 3 C atoms, vinyl, ethynyl, halogen, an alkoxy having from 1 to 6 C atoms, a difluoroalkoxy with the alkyl having from 1 to 7 C atoms, an alkoxymethyloxy having from 1 to 7 C atoms, an alkylthiomethyloxy with the alkyl having from 1 to 7 C atoms, an alkylmethylthio with the alkyl having from 1 to 7 C atoms, cyano, difluoromethylthio, a substituted phenyl- or phenylalkyl with the alkyl having from 1 to 8 C atoms; preferably $R_{IV-II}$ is CH₃O, $R_{IVd}$ is H and $R_{IVd1}$ is CH₃, and is known as the residue of naproxen;
X=NH and $X_1$ is equal to (CH₂)₄ or (CH₂CH₂O)₂; also preferred is the same compound where X is equal to O;
in the compounds of formula (X), for which the residue of loxoprofen has been shown, the residues described in U.S. Pat. No. 4,161,538 herein incorporated by reference can be used as equivalents; preferred are the compounds where $R_{IVd}$ is H and $R_{IVD1}$ is CH₃, X=NH and $X_1$ is equal to (CH₂)₄ or (CH₂CH₂O)₂; also preferred is the same compound where X is equal to O;
in the compounds of formula (III):
$R_{IV-III}$ is a C₂-C₅ alkyl, even branched whenever possible, a C₂ and a C₃ alkyloxy, allyloxy, phenoxy, phenylthio, a cycloalkyl having from 5 to 7 C atoms, optionally substituted at position 1 by C₁-C₂ alkyl;
preferred is the compound where $R_{IV-III}$ is $$\begin{array}{c}CH_3\\ \diagdown\\ CH-CH_2-\\ \diagup\\ CH_3\end{array}$$

and $R_{IVd}$=H, $R_{IVd1}$ is CH₃, a compound known as the residue of ibuprofen; X=NH and $X_1$ is equal to (CH₂)₄ or (CH₂CH₂O)₂; also preferred is the same compound where X is equal to O;

Group IV A)

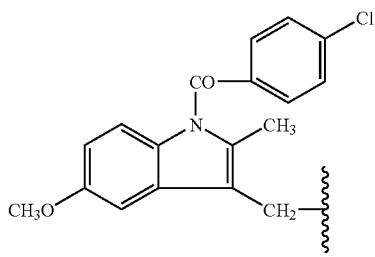
(IV)

where A=RCOO, t=1, of which the residue of the known indomethacin has been shown, its equivalents as described and obtained in patent U.S. Pat. No. 3,161,654 herein incorporated by reference can be used;

Group V A) chosen from the following:

V Aa) fenamates chosen from the following, where t=1

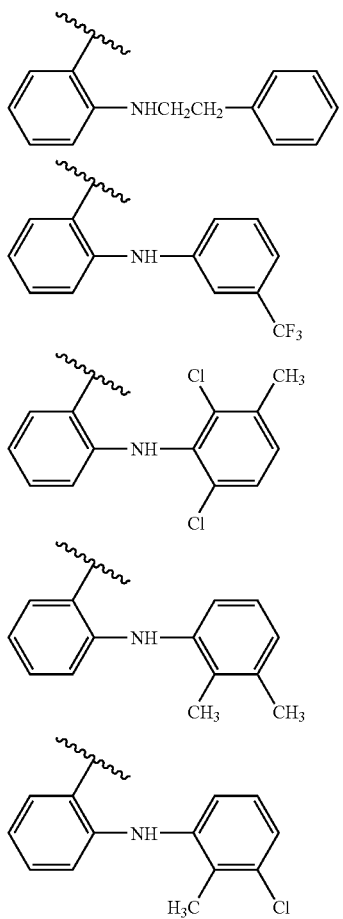
(V Aa1)
(V Aa2)
(V Aa3)
(V Aa4)
(V Aa5)

V Ab), derivatives of niflumic acid, where t=1:

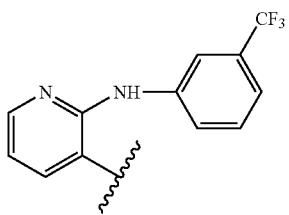
(V Ab1)

V Ac), COX$_2$ inhibitors, where t=0 and R is as follows:

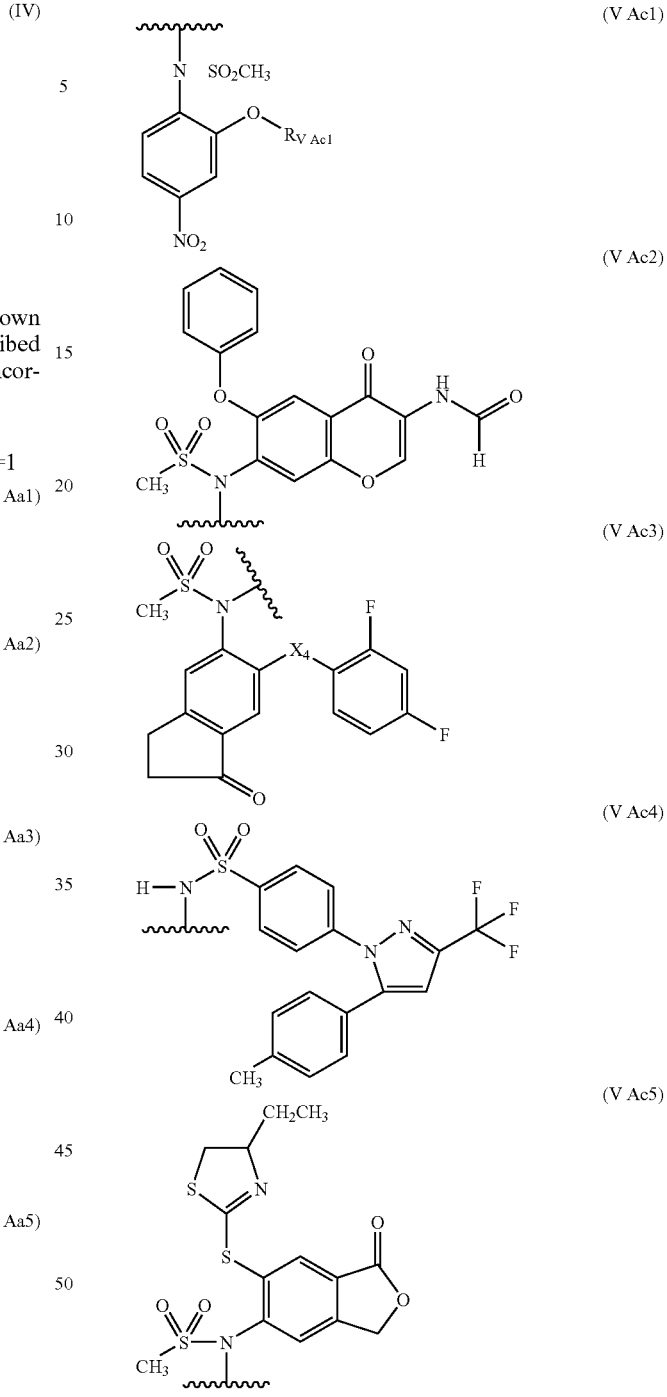
(V Ac1)
(V Ac2)
(V Ac3)
(V Ac4)
(V Ac5)

V Ad) Derivatives of diuretics when t=1 and R is as follows:

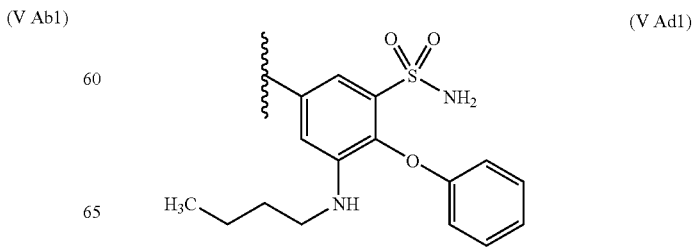
(V Ad1)

-continued (V Ad2)

(V Ad3)

(V Ad4)

V Ae) Derivative of diuretics when t=0 and R is as follows:

(V Ae1)

(V Ae2)

(V Ae3)

(V Ae4)

-continued (V Ae5)

(V Ae6)

(V Ae7)

(V Ae8)

(V Ae9)

(V Ae10)

(V Ae11)

(V Ae12)

where the meaning in group V A) is as follows:

in V Aa):

in compounds (V Aa1) the residue of enfenamic acid, 2-[(2-phenylethyl)amino]benzoic acid, where COOH was substituted according to the present invention, has been shown.

This can be prepared according to the Indian patents 103.066 and 114.805, herein incorporated by reference. Equivalent products containing various substituents as described in said patents can be used, too.

In compounds (V Aa2) the residue of flufenamic acid, 2-[[3-(trifluoromethyl)phenyl]-amino]benzoic acid, where COOH was substituted according to the present invention, has been shown.

This can be prepared according to Wilkinson's article, Finar, J.Chem.Soc. 1948, 32, herein incorporated by reference. Any equivalent product containing various substituents as described in said article can be used, too.

In compounds (V Aa3) the residue of meclofenamic acid, 2-[(2,6-dichloro-3-methylphenyl)amino]benzoic acid where COOH was substituted according to the present invention, has been shown.

This can be prepared according to the German patent DE 1.149.015 and U.S. Pat. No. 3.313.848 herein incorporated by reference. Any equivalent product containing various substituents as described in said patents can be used, too.

In compounds (V Aa4) the residue of mefenamic acid, 2-[(2,3-dimethylphenyl)amino]benzoic acid where COOH was substituted according to the present invention, has been shown.

This can be prepared according to the Belgian patent 605.302, herein incorporated by reference. Any equivalent product containing various substituents as described in said patent can be used, too.

In compounds (V Aa5) the residue of toltenamic acid, 2-[(3-chloro-2-methylphenyl)amino]benzoic acid where COOH was substituted according to the present invention, has been shown.

This can be prepared according to patent U.S. Pat. No. 3,313,848, herein incorporated by reference. Any equivalent product containing various substituents as described in said patent can be used, too.

In V Ab):

in compounds (V Ab1) the residue of niflumic acid, 2-[[3-(trifluoromethyl)phenyl]amino]-3-pyridine carboxylic acid, where COOH was substituted according to the present invention, has been shown.

This can be prepared according to patent U.S. Pat. No. 3,415,834, herein incorporated by reference. Any equivalent product containing various substituents as described in said patent can be used, too.

In V Ac):

in compound (V Ac1)$R_{vac1}$ attached to the oxygen atom in position 2 of the benzene ring of N-(4-nitrophenyl) methansulphonamide can be phenyl or cycloexane. When $R_{vac1}$ is phenyl the residue is that of nimesulide.

This can be prepared according to patent U.S. Pat. No. 3,840,597 herein incorporated by reference. Any equivalent product containing various substituents as described in said patent can be used, too.

In compounds (V Ac2) the residue of 3-formylamino-7-methylsulfonylamino-6-phenoxy -4H-1-bezopyran-4-one was substituted according to the present invention, has been shown.

This can be prepared according to patent DE 3834204 herein incorporated by reference. Any equivalent product containing various substituents as described in said patent can be used, too.

In compounds (V Ac3) the atom $X_4$ that links the radical 2,4-difluorothiophenyl to position 6 of the indanone ring of the residue 5-methanesulfonamido-1-indanone can be sulfur or oxygen.

This can be prepared according to WO 9413635 herein incorporated by reference. Any equivalent product containing various substituents as described in said patent can be used, too.

In compounds (V Ac4) the residue of celecoxib 4-[5(4-methylphenyl)-3-(trifluoromethyl)pyrazol-1-yl] benzensulphonamide was substituted according to the present invention, has been shown.

This can be prepared according to patent WO 9427980 herein incorporated by reference. Any equivalent product containing various substituents e.g. WO 9515315-318 as described in said patents can be used, too.

In compounds (V Ac5) the residue of 6-[2-(3-ethyl-2,3-dihydro-thiazolyl)thio-5-methansulphonamido-3H-isoben-zonfuran-1-one was substituted according to the present invention, has been shown.

This can be prepared according to patent WO 9623786 herein incorporated by reference. Any equivalent product containing various substituents as described in said patent can be used, too.

In compounds (v Ad1) the residue of bumetanide 3-(Aminosulfonyl)-5-(butylamino)-4-phenoxybenzoic acid was substituted according to the present invention, has been shown.

This can be prepared according to patent U.S. Pat. No. 3,806,534 herein incorporated by reference. Any equivalent product containing various substituents as described in said patent can be used, too.

In compounds (V Ad2) the residue of ticrynafen [2,3-Dichloro-4-(2-thienylcarbonyl)-phenoxy]acetic acid was substituted according to the present, has been shown. This can be prepared according to patent U.S. Pat. No. 3,758,506 herein incorporated by reference. Any equivalent product containing various substituents as described in said patent can be used, too.

In compounds (VAd3) the residue of ethacrynic acid [2,3-Dichloro-4-(2-methylene-1-oxobutyl)phenoxy]acetic acid was substituted according to the present invention, has been shown.

This can be prepared according to patent U.S. Pat. No. 3,255,241 herein incorporated by reference. Any equivalent product containing various substituents as described in said patent can be used, too.

In compounds (V Ad4) the residue of piretanide 3-(Aminosulfonyl)-4-phenoxy-5-(1-pyrrolidinyl)benzoic acid was substituted according to the present invention, has been shown.

This can be prepared according to patent U.S. Pat. No. 4,010,273 herein incorporated by reference. Any equivalent product containing various substituents as described in said patent can be used, too.

In compounds (V Ae1) the residue of tripamide (3aα, 4α, 7α,7aα)-3-(Aminosulphonyl)-4-chloro-N-octaidro-4,7-methano-2H-isoindol-2-yl)benzamide was substituted according to the present invention, has been shown.

This can be prepared according to patent JP 73 05, 585 herein incorporated by reference. Any equivalent product containing various substituents as described in said patent can be used, too.

In compounds (V Ae2) the residue of torsemide N-[[(1-Methylethyl)amino]carbonyl]4-[(3-methylphenyl) amino]-3-pyrinesulfonamide was substituted according to the present invention, has been shown.

This can be prepared according to patent U.S. Pat. No. 4,018,929 herein incorporated by reference. Any equivalent product containing various substituents as described in said patent can be used, too.

In compounds (V Ae3) the residue of azosemide 2-Chloro-5-(1H-tetrazol-5-yl)-4-[(2-thienylmethyl)amino]benzensulphonamide was substituted according to the present invention, has been shown.

This can be prepared according to patent U.S. Pat. No. 3,665,002 herein incorporated by reference. Any equivalent product containing various substituents as described in said patent can be used, too.

In compounds (V Ae4) the residue of bendroflumethiazide 3,4-Dihydro-3-(phenyl-methyl)-6-(trifluoromethyl)-2H-1,2,4-benzothiadiazine-7-sulfonamide 1,1-dioxide was substituted according to the present invention, has been shown.

This can be prepared according to patent U.S. Pat. No. 3,392,168 herein incorporated by reference. Any equivalent product containing various substituents as described in said patent can be used, too.

In compounds (V Ae5) the residue of chlorothiazide 6-Chloro-2H-1,2,4-benzothiadizine-7-sulfonamide 1,1-dioxide was substituted according to the present invention, has been shown.

This can be prepared according to patent U.S. Pat. No. 2,809,194, U.S. Pat. No. 2,937,169 herein incorporated by reference. Any equivalent product containing various substituents as described in said patent can be used, too.

In compounds (V Ae6) the residue of hydrochlorotiazide 6-Chloro-3,4-dihydro-2H-1,2,4-benzothiadiazine-7-sulfonamide 1,1-dioxide was substituted according to the present invention, has been shown.

This can be prepared according to patent DE 1,163,332, U.S. Pat. No. 3,043,840 herein incorporated by reference. Any equivalent product containing various substituents as described in said patent can be used, too.

In compounds (V Ae7) the residue of methyclothiazide (6-Chloro-3-(chloromethyl)-3,4-dihydro-2-methyl-2H-1,2,4-benzothiadiazine-7-sulfonamide 1,1-dioxide was substituted according to the present invention, has been shown.

This can be prepared according to patent Close et al., J.Am.Chem.Society 82, 1132 (1960) herein incorporated by reference. Any equivalent product containing various substituents as described in said patent can be used, too.

In compounds (V Ae8) the residue of chlorthalidone 2-Chloro-5-(2,3-dihydro-1-hydroxy-3-oxo-1H-isoindol-1-yl)benzensulfonamide was substituted according to the present invention, has been shown.

This can be prepared according to patent U.S. Pat. No. 3,055,904 herein incorporated by reference. Any equivalent product containing various substituents as described in said patent can be used, too.

In compounds (V Ae9) the residue of Indapamide 3-(Aminosulfonyl)-4-chloro-N-(2,3-dihydro-2-methyl-1H-indol-1-yl)benzamide was substituted according to the present invention, has been shown.

This can be prepared according to patent U.S. Pat. No. 3,565,911 herein incorporated by reference. Any equivalent product containing various substituents as described in said patent can be used, too.

In compounds (V Ae10) the residue of metolazone 7-Chloro-1,2,3,4-tetrahydro-2-nethyl-3-(2-methylphenyl)-4-oxo-6-quinazolinesulfonamide was substituted according to the present invention, has been shown.

This can be prepared according to patent U.S. Pat. No. 3,360,518 herein incorporated by reference. Any equivalent product containing various substituents as described in said patent can be used, too.

In compounds (V Ae11) the residue of quinetazone 7-Chloro-2-ethyl-1,2,3,4-tetrahydro-4-oxo-6-quinazolinesulfonamide was substituted according to the present invention, has been shown.

This can be prepared according to patent U.S. Pat. No. 2,976,289 herein incorporated by reference. Any equivalent product containing various substituents as described in said patent can be used, too.

In compounds (V Ae12) the residue of furosemide 5-(Aminosulfonyl)-4-chloro-2-[(2-furanylmethyl)amino]benzoic acid was substituted according to the present invention, has been shown.

This can be prepared according to patent U.S. Pat. No. 3,058,882 herein incorporated by reference. Any equivalent product containing various substituents as described in said patent can be used, too.

The compounds under V Ad/V Ae are particularly suitable for the treatment of urinary disorders, in particular of anuresis.

$X_1$, in formula $A-X_1—NO_2$, is a bivalent-connecting bridge chosen from the following:

YO where Y is a linear or whenever possible branched $C_1$-$C_{20}$ alkylene, preferably having from 2 to 5 carbon atoms, or an optionally substituted cycloalkylene having from 5 to 7 carbon atoms;

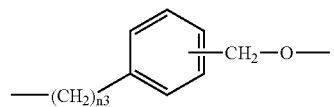

where $n_3$ is an integer from 0 to 3;

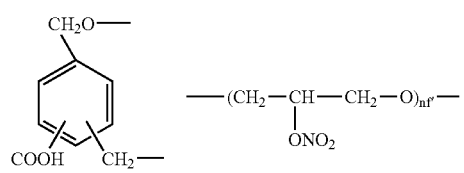

where nf is an integer from 1 to 6, preferably from 2 to 4;

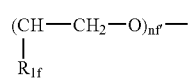

wherein $R_{1f}$=H, $CH_3$ and nf is an integer from 1 to 6, preferably from 2 to 4.

The processes for obtaining the compounds which contain R from groups I A-IV A are described in patent application WO 95/30641 herein incorporated by reference.

The processes for preparing the compounds of class V A are those described above in application WO 95/30641.

The products of the invention are therapeutically useful in the treatment of various forms of urinary incontinence at lower doses than the corresponding precursor products without the NO donor group and with a wider activity spectrum and without causing the disadvantage previously described for this kind of precursors.

It has been surprisingly found by the Applicant that, meaningfully, the products of the invention do not show reduced pharmacological activity compared to precursors. Conversely, they have a wider pharmacological range of action, since a synergy between the cyclooxigenase inhibiting effect and the myorelaxing effect related to the opening of potassium channels and/or release of nitric oxide, was unexpectedly observed in the lower urinary tract. The products of the invention exhibit a higher safety and do not induce tachyphylaxis.

Additionally, the Applicant found that the products of the invention carry out a pharmaco-therapeutic activity in diverse appropriate experimental models, as described below:
articular inflammation (musculoskeletal disease) in rats; see Winter C. et al., *Caraggeenin-induced edema in hind paw of the rat as an assay for antiinflammatory drugs*, Proceedings of the Society for Experimental Biology and Medicine 1962, 111, 544-47;
respiratory disease for example bronchospasm from bradykinin in Guinea pigs (Del Soldato P. et al., *The anesthetized Guinea pig as a versatile pharmacological test object*, Jour. of Pharmacological Methods, 1981 5, 279-285);
vascular disease, such as re-stenosis induced in rats (Role of kinins and nitric oxide in the effects of anigiotensin converting enzyme inhibitors on neointima formation, Fahry-RD et al., CIRC-RES. 72/6 (1202-1210)1983);
gynaecological and obstetrical diseases:
as shown in hyperexcitability states in rat isolated myometrium (Izumi H. et al., *Gestational changes in L-arginine-induced relaxation of pregnant rat and nonpregnant myometrial contractility*, Am. J. Obstet. Gynecol., 1993, 169, 1327-1337);
blood platelet aggregation in women in a pre-eclampsia condition (Janes Sl et al., *Flow cytometric detection of circulating activated platelets and platelet hyper-responsiveness in pre-eclampsia and pregnancy*, Clin. Science, 86, 731-739, 1994).
intestinal tumours, such as for example in experimental adenocarcinoma in rats (Dubois R. et al., *Increased cyclooxigenase-2 levels in carcinogen-induced rat colonic tumors*, Gastroenterology, 110,1259-1262, 1996).

Therefore, based on the experimental results obtained the above products may be therapeutically useful in the following diseases, in addition to urinary incontinence:
musculoskeletal disease of an inflammatory nature: group V A;
respiratory disease, for example bronchitis, in particular asthma, etc.: compounds of the groups from I A to V A;
gynaecological and obstetricial diseases, including premature delivery, pre-eclampsia and dysmenorrhoea: groups from I A to V A and, additionally, the comopounds from group VI A as defined below;
vascular disease such as re-stenosis: compounds from groups I A to VI A;
gastrointestinal tumour: compounds from groups from I A to VI A.

The compounds in group VI A, where t=1, include the following:

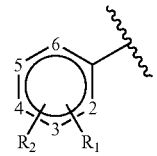

(Ia)

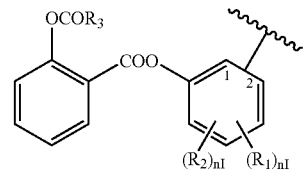

(Ib)

where:
$R_1$ is $OCOR_3$; where $R_3$ is methyl, ethyl or a linear or branched $C_3$-$C_5$ alkyl, or the residuee of a single-ring heterocycle having 5 or 6 atoms which can be aromatic, partially or totally hydrogenated, containing one or more heteroatoms independently chosen from O, N and S;

$R_2$ is hydrogen, hydroxy, halogen, a linear or whenever possible branched alkyl having from 1 to 4 C atoms, a linear or whenever possible branched alcoxyl having from 1 to 4 C atoms; a linear or whenver possible branched perfluoroalkyl having from 1 to 4 C atoms, for example trifluoromethyl, nitro, amino, mono-or di($C_{1-4}$)alkylamino;

$R_1$ and $R_2$ jointly are the dioxymethylene group, with the proviso that when X=NH, then $X_1$ is ethylene and $R_2$=H; $R_1$ cannot be $OCOR_3$ at position 2 when $R_3$ is methyl; nI being an integer from 0 to 1;

preferably in Ia), X is equal to O or NH, $R_1$ is acetoxy, preferably at position 3 or 4, most preferably in the ortho position to CO. $X_1$ is ethylene or $(CH_2CH_2O)_2$, $R_2$ is hydrogen or halogen, most preferred are the following A $X_1$ $NO_2$ compounds: 3-acetoxy-N-(2-nitroxyethyl)-benzamide, 4-acetoxy-N-(2-nitroxyethyl)-benzamide, 3-acetoxy-N-(5-nitroxypenthyl)-benzamide, 2-acetoxy-N-(5-nitroxypenthyl)-benzamide, N-2-(nitroxyethyl)-2-propionoxybenzamide, 2-acetoxy-2-nitro-xyethylbenzoate, 2-acetoxy-N-(cis-2-nitroxycyclohexyl)-benzamide, 2-acetoxy-4-chloro-N-(2-nitroxyethyl)-benzamide, N-(2-nitroxyethyl)-2-((4-thiazolindinyl) carbonyloxy)-benzamide hydrochloride, 2-nicotinoyloxy-N-(2-nitroxyethyl)-benzamide, 2-acetoxy-5-nitroxypenthylbenzoate;

preferably in Ib) $R_3$=$CH_3$, nI=0;

X is equal to O, $X_1$ is ethylene; in this case Ib) is the residue of acetylsalicylsalicylic acid.

The processes to obtain the compounds which contain R in group VI A are described in patent WO 95/30641 herein incorporated by reference.

The examples below are intended as an explanation not a limitation of the present invention.

EXAMPLES

Examples 1,2,3 and From 1A to 1F (Comparison)

Chemical Synthesis

The following compounds were prepared: NO-indomethacin (NO-I), NO-flufenamic (NO-F), NO-nimesulide (NO-M), NO-Naproxen (NO-N).

Preparation of NO-Indomethacin (NO-I)

| | |
|---|---|
| 3-Hydroxybenzylnitrate | 9.5 g |
| Indomethacin | 7.4 g |
| Dicyclohexylcarbodiimide | 5.6 g |
| $CH_2Cl_2$ | 200 ml | were reacted and the solution was allowed to react overnight at zoom temperature, concentrated to a small volume and filtered. The filtrate was dried and passed through a column containing gel by using chloroform/ethyl acetate 14:1 as an eluting system. A head fraction was thus separated and purified by chromatography using a 2-mm silica plate. Each plate was run three times in a mobile phase made up of cyclohexane/ethyl acetate 6:1.

A yield of 85% was obtained of indomethacin-NO in group IV A where R is residue (IV) of indomethacin; t=1; X=O; and $X_1$ is the connecting bridging, shown after YO, where n3=0, and having the general formula:

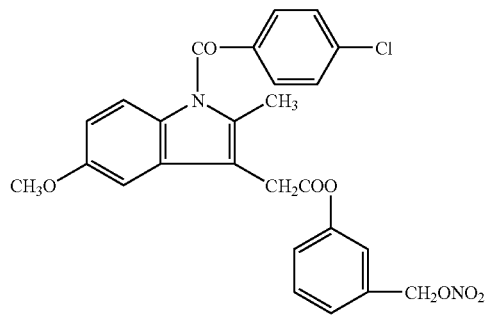

Preparation of NO-Flufenamic (NO-F)

| | |
|---|---|
| 3-Hydroxybenzylnitrate | 6 g |
| Flufenamic acid | 13 g |
| Dicyclohexylcarbodiimide | 9.5 g |
| $CH_2Cl_2$ | 150 ml |
| Ethyl ether | 50 ml | were reacted and it was allowed to react overnight, concentrated to a small volume and dicyclohexylurea was filtered. The filtrate was dried and passed through a column containing silica by using $CH_2Cl_2$ as an eluant. A head fraction was thus separated. This fraction was purified by chromatography using a 2-mm silica plate and a cyclohexane/ethyl acetate 6:1 system. Each plate was run three consecutive times. The head fraction was recovered by extraction with ethyl ether. The ethereal extract was brought to dryness and gives a yellow oil and a yield of 80% for flufenamic-NO.

The $^1$H NMR analysis ($CDCl_3$, 200 MHz) gave the following data: 5.5 (2H, s); 6.9 (1H, t); 7.4 (1OH, m); 8.2 (1H, dd). The product obtained has the formula:

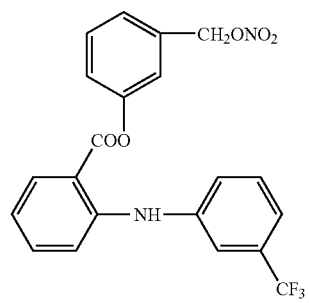

Preparation of No-Nimesulide (NO-M)

Preparation of the Brominated Derivative

N-[(2-PHENOXY-4-NITRO)PHENYL]-N-(6-BROMO) HEXANOYLMETHANE-SULPHONAMIDE 4,85 g 6-Bromohexanoylchloride (23 mmol) was added dropwise to a mixture kept at 0° C. of 7 g nimesulide (23 mmol) and 6.4 ml triethylamine (46 mmol) in dichloromethane (80 ml). After stirring for one hour at 0° C., a thin layer chromatography analysis (eluant: toluene/ethyl acetate 9:1) showed that unreacted nimesulide was still present. 1 g acyl chloride (4.7 mmol) and 3 ml triethylamine (22 mmol) were added to the reaction mixture, the temperature was allowed to rise to room temperature and the reaction mixture was stirred overnight. A chromatographic control showed that the reaction was complete. The reaction mixture was treated with water (50 ml), the organic phase was then washed three times with water (50 ml for each washing), then with diluted $N_aCH$ (5% w/v), then dried over anhydrous sodium sulphate (10 g). Solvent evaporation at reduced pressure left a yellow solid residue which was ground twice with two portions of ethyl ether (50 ml each). The air-dried solid was 8.3 g, which corresponds to a yield of 74% and exhibited a melting point of 98° C.

Preparation of NO-Nimesulide (NO-M)

N-[(2-PHENOXY-4-NITRO)PHENYL]-N-(6-NITROXY) HEXANOYLMETHANE-SULPHONAMIDE

A solution of 4 g N-[(2-phenoxyl-4-nitro)phenyl]-N-(6-bromo)hexanoyl-methanesulphonamide (8.24 mmol) and 2.8 g silver nitrate (16.48 mmol) in anhydrous acetonitrile (20 ml) was reacted with stirring for 2 days. Then 1 g of silver nitrate (6 mmol) was then added and stirring was continued for another day. The precipate was removed by filtration and the solvent was evaporated from the filtrate at reduced pressure. The residue was dissolved in a mixture of equal proportions of ethyl acetate and isopropyl ether and stirred for a few minutes with chromatographic-grade silica gel (5 g). The solid was removed by filtration and the filtrate of the solvent was removed at reduced pressure. The residue was a yellow oil which solidified in time (2.6 g). The solid was ground with ethyl ether and dried, and exhibited a melting point of 96° C.

The $^1$H NMR spectrum ($CDCl_3$) showed the following signals: 8.05 (1H, m); 7.62 (2H, m); 7.48 (2H, m); 7.32 (1H, m); 7.08 (2H, m); 4.40 (2H, t); 3.40 (3H, s); 2.24 (2H, t) 2.18 (3H, s); 1.70 (4H, m); 1.45 (2H, m).

Preparation of Compound NO-Naproxen (NO-N)

Compound NO-Naproxen was prepared according to Example 1h (Example 1) in patent WO 95/30641.

Pharmacological Tests

The products were administered in a suspension of carboxymethyl cellulose in in-vivo experiments, while they were dissolved in dimethylsulphoxide in in-vitro studies.

The same vehicle used in the corresponding treatment groups was always used for control groups.

The acute toxicity was roughly determined administering an oral dose of 50 mg/kg of substance to groups of 10 mice. Death rate and appearance of toxic symptoms were evaluated in a period of 14 days from dosing: no toxic effects were observed at the dose administered.

Contraction Inhibiting Activity in Isolated Rat Detrusor

Male Wistar rats weighing 200 to 300 g were used. The method used is described by Zhou Q. et al. (1995) (see Example 13). After sacrificing the rats by cervical displacement the urinary bladder was isolated and horizontal strips of detrusor muscle about 2 mm wide and about 5 mm long were obtained from the median region. The strips were placed in baths for isolated organs containing Krebs liquid and subjected to a 1 g tension. Tension variations during the test were measured isometrically by using a pressure transducer connected to a polygraph. The inhibitory effect of a pre-treatment with the test derivatives on contraction induced by 40 mM KCl was determined versus drugs having an opening potassium channel activity (cromakalin, nicorandil) nitroderivatives (nitroglycerin, nicorandil) and anti-inflammatories (indomethacin, naproxen, nimesulide). The results are shown in Table 1.

TABLE 1

| Example | Product | No. of tests | Inhibition % |
|---|---|---|---|
| 1A comparison | Cromakalim $10^{-6}$ M | 10 | 33.3 |
| 1B comparison | Nitroglycerin $10^{-5}$ M | 10 | 28.7 |
| 1C comparison | Nicorandil $10^{-4}$ M | 10 | 26.4 |
| 1D comparison | Indomethancin $10^{-4}$ M | 10 | 38.5 |
| 1E comparison | Naproxen $5 \cdot 10^{-4}$ M | 10 | 15.2 |
| 1F comparison | Nimesulide $10^{-4}$ M | 10 | 41.8 |
| 1 | NO-I $10^{-4}$ M | 10 | 46.3 |
| 2 | NO-N $5 \cdot 10^{-4}$ M | 10 | 31.3 |
| 3 | NO-M $10^{-4}$ M | 10 | 48.1 |

All new nitroderivatives (Examples 1 to 3) proved to be more active than the products used as comparison.

Examples 4-5 and 4A-4C (Comparison)

In Vivo Studies in Normal Urinary Bladder of Conscious Rats

Cystometrograms of conscious rats were determined according to the method described by Howe B. B et al. (1995) (see Example 9).

Male Wistar rats weighing about 500 g were used. The rats were anaesthetised with Nembutal. After opening their abdomen and exposing their urinary bladder, a catheter filled with physiological solution was implanted in the urinary bladder and caused to emerge from the back of the animals. The abdominal muscle and skin were then sutured. 48 hours after surgery the animals were placed in metabolic cages and the catheters were connected to a perfusor which perfused 0.18 ml/min of a physiological solution into the urinary bladder, and to a pressure transducer in order to measure intravesical pressure. After stabilisation for 60 minutes, the animals were orally treated with the test products and urination frequency was than measured during 4 hours after dosing. Table 2 shows the results obtained expressed as a ratio versus the baseline frequency recorded before dosing IC=interval between contractions).

TABLE 2

| Example | Treatment | No. of tests | IC treated/IC baseline |
|---|---|---|---|
| 4 A | Controls | 8 | 1.05 |
| 4 B comparison | Flufenamic acid 5 mg/kg | 8 | 1.42 |
| 4 | NO-F 5 mg/kg | 8 | 1.62 |
| 4 C comparison | Indomethancin 5 mg/kg | 8 | 1.34 |
| 5 | NO-I 5 mg/kg | 8 | 1.48 |

Both new derivatives (Examples 4-5) proved to be more active than the products used as comparison.

Examples 5-6 and 5A-5B (Comparison)

In Vivo Studies in Normal Urinary Bladders of Anaesthetised Rats

40 Sprague Dawley rats weighing about 300 g were randomly divided into 4 groups and orally treated twice a day for 4 days according to the following experimental scheme:

| 1. Controls: | 0.5% carboxymethyl cellulose |
| 2. Indomethacin | 3 mg/kg |
| 3. NO-I | 3 mg/kg |
| 4. NO-F | 5 mg/kg |

18 hours after the last treatment, the effects on the urinary bladder voiding reflex were evaluated using the method described by Maggi C. A. et al., *Prostanoids modulate reflex micturition by acting through capsaicin-sensitive afferents*, European Journal of Pharmacology, 105-112, 1988.

The animals were anaesthetised with urethane, the urinary bladder was prepared for intraluminal pressure measurement. After a stabilisation period with an empty urinary bladder, this was progressively filled with a physiological solution by slow infusion (0.046 ml/min). A contraction of the urinary bladder was observed upon reflex triggering.

The volume of physiological solution and intraluminal pressure required to evoke the reflex (volume and pressure thresholds) were measured. Table 3 shows the pressure and volume threshold values after treatment, calculated considering 100 the values obtained in control animals. All tested products increased this threshold and can, therefore, be considered useful in case of detrusor instability.

TABLE 3

| Example | Treatment | No. of animals | Pressure threshold (%) | Volume threshold (%) |
|---|---|---|---|---|
| 5 A | Controls | 10 | 100 | 100 |
| 5 B | Indomethacin | 10 | 190 | 198 |
| 5 | NO-l | 10 | 223 | 226 |
| 6 | NO-F | 10 | 203 | 205 |

Examples 7-8 (7A-7D as Comparison)

In Vitro Studies in Unstable Urinary Bladder

The vesical hypertrophy model secondary to urethral obstruction in rats described by Malmgren A. et al.: *Cystometrical evaluation of bladder instability in rats with intravesical outflow obstruction*, The Journal of Urology, 1987, 137, 1291-1294, was used in order to evaluate the effect of the drugs on hyperactive vesical muscle.

Male Sprague Dawley rats weighing about 250 g were used. In order to obtain partial urethral obstruction, the rats were anaesthetised with Nembutal and the urinary bladder and urethra were exposed by abdominal incision. A ligature was made around the urethra in the presence of an intraluminal cannula with 1 mm diameter. After suturing the abdominal wall the animals were stabulated for 6 weeks in order for vesical hypertrophy to start.

The in vitro experiments were conducted with the parallel use of strips obtained from normal rats and rats with vesical hypertrophy.

The in vitro urinary bladder strips were prepared as described above and the inhibition induced by the drugs on contraction induced by $1/7$ Hz electrical stimulation lasting 1 msec., an above maximal voltage, produced by two platinum electrodes, was measured.

The following table shows the percentage of contraction induced by electrical stimulus in normal and hypertrophic urinary bladders in the presence of the test drugs.

TABLE 4

| Example | Product/Tissue | No. of tests | Contraction % |
|---|---|---|---|
| 7 A | Cromakalim $10^{-6}$ M (normal) | 6 | 50.5 |
| 7 B | Cromakalin $10^{-6}$ M (hypertrophic) | 6 | 35.7 |
| 7 C | Indomethacin $10^{-6}$ M (normal) | 6 | 78.2 |
| 7 D | Indomethacin $10^{-6}$ M (hypertrophic) | 6 | 76.3 |
| 7 | NO-I $10^{-6}$ M (normal) | 6 | 61.5 |
| 8 | NO-I $10^{-6}$ M (hypertropic) | 6 | 40.3 |

Differently from indomethacin, the products with an opening of potassium channel activity and the new compounds were found to be more active in inhibiting hypertrophic urinary bladder contraction than normal urinary bladder.

Examples 9-10 and From 9A to 9B (Comparison)

In Vivo Studies in Normal Urinary Bladder of Conscious Dogs

The cystometrogram of conscious dogs was determined in accordance with the method described by Howe B. B. et al., *ZENECA ZD 6169: a NOVEL $K_{ATP}$ Channel opener with in vivo selectivity for urinary bladder*, Journal of Pharmacology and Experimental Therapeutics, 274, 884-890, 1995.

Female Beagle dogs with urinary bladder catheterised through the urethra by operating in sterile conditions, were used. Catheters were connected to a perfusor which perfused into the urinary bladder a physiological solution and to a pressure transducer in order to measure intravesical pressure. After 15 minute stabilisation, a 30 ml bolus of physiological solution was perfused into the urinary bladder in order to measure increased intravesical pressure and a series of smaller boluses were then perfused until spontaneous contractions were observed. After a period of contraction stabilisation, contracting activity was monitored for 60 minutes.

The animals were then treated orally with the test products and urination frequency was then measured during 4 hours following dosing in control rats and treated rats. Table 5 shows the results obtained expressed as a ratio versus the baseline frequency recorded before dosing (IC=interval between contractions).

TABLE 5

| Examples | Treatment | No. of animals | IC treated/IC baseline |
|---|---|---|---|
| 9 A comparison | Controls | 5 | 1.03 |
| 9 B comparison | Cromakalim 0.5 mg/kg | 5 | 1.48 |
| 9 C comparison | Flufenamic acid 3 mg/kg | 5 | 1.42 |
| 9 | NO-F 3 mg/kg | 5 | 1.76 |
| 9 D comparison | Indomethacin 3 mg/kg | 5 | 1.25 |
| 10 | NO-I 3 mg/kg | 5 | 1.43 |

Examples 11-12 and 11A-11D (Comparison)

Relaxing Effect in Pig Urethral Smooth Muscle

The method described by Werkstrom et al., *Factors involved in the relaxation of female pig urethra evoked by electrical field stimulation*, British Journal of Pharmacology, 116, 1599-1604, 1995, was used for sample preparation. Samples of urethra were removed from female pigs about 6 months old.

The urethra was opened longitudinally and samples of smooth muscle about 1×2×6 mm in size were removed from an area about 4 mm below ureteral orifices. The samples of smooth muscle were placed in baths for isolated organs, incubated at 37° C. and subjected to a 10 mN tension and connected to a force transducer for measuring mechanical activity. After a period of balancing of about 60 minutes, the prepared samples were exposed to Krebs solution without $Ca_{++}$ to determine the highest relaxation level. Normal tone was then restored by adding Krebs solution. The relaxation effects of the test derivatives were then measured. The test wasa repeated two consecutive times for each prepared sample in order to evaluate any tachyphylaxis effects. The table below shows the relaxation percentages obtained following the two treatments with each test product, expressed considering 100% the highest relaxation determined by the medium out $Ca^{++}$.

TABLE 6

| Example | Product | No. of tests | Relaxation % 1 | Relaxation % 2 |
|---|---|---|---|---|
| 11 A | Indomethacin $10^{-5}$ M | 6 | 1.0 | 1.2 |
| 11 | NO-I $10^{-5}$ M | 6 | 39.3 | 37.2 |
| 11 B | Flufenamic acid $10^{-5}$ M | 6 | 12.2 | 13.2 |
| 12 | NO-F $10^{-5}$ M | 6 | 45.8 | 52.1 |
| 11 C | Nitroglycerin $10^{-5}$ M | 6 | 32.1 | 7.3 |
| 11 D | L-arginine $10^{-5}$ M | 6 | 22.7 | 12.2 |

The results show that, while drugs with an anti-inflammatory activity such as indomethacin were practically inactive except for flufenamic acid which has itself a myorelaxing activity, and conventional NO donors, such as nitroglycerin and arginine, were active but induced tachyphylaxis, the new derivatives which are an object of the invention were active and did not induce any tachyphylaxis.

Examples 13-15 and 13A-13B (Comparison)

Relaxing Activity on Vessel Smooth Muscle

Male Wistar rats weighing 200 to 300 g were used. The method used is described by Zhou Q. et al. *The inhibitory mechanism of nicorandil in isolated rat urinary bladder and femoral artery*, European Journal of Pharmacology, 153-159, 1995. After sacrifing the rats by cervical displacement, the femoral arteries were isolated for the preparation of helicoidal strips about 1×15 mm in size, from which the endothelium was removed. The prepared strips were placed in baths for isolated organs containing Krebs liquid and subjected to a weight of 0.5 g. Tension variations during the test were isometrically measured by means of a pressure transducer connected to a polygraph. The inhibitory effect of a treatment with the test derivatives on contractions induced by $3 \times 10^{-5}$ M phenylephrine versus reference preparations having a potassium channel opening activity and/or NO donors was measured.

The results are included in Table 7.

TABLE 7

| Example | Product | No. of tests | Inhibition % |
|---|---|---|---|
| 13 A comparison | Cromakalim $3 \times 10^{-7}$ M | 10 | 54.1 |
| 13 B comparison | Nicorandil $10^{-6}$ M | 10 | 32.6 |
| 13 | NO-I $10^{-4}$ M | 10 | 22.2 |
| 14 | NO-N $5 \cdot 10^{-4}$ M | 10 | 29.0 |
| 15 | NO-M $10^{-4}$ M | 10 | 19.5 |

All new compounds proved to be less active than Cromakalin and Nicorandil, even used at higher concentrations, then those shown in specific models (see for example Table 6).

Example 16-17 and 16A-16B (Comparison)

In Vivo Gastrointestinal Safety Studies

Forty Sprague Dawley rats weighing about 300 g were randomly divided into 4 groups and orally treated twice a day for 4 days according to the following experimental scheme:

| | |
|---|---|
| 1. Controls: carboxymethyl cellulose (0.5% by weight): | (5 ml/kg) |
| 2. Indomethacin | 3 mg/kg |
| 3. NO-I | 3 mg/kg |
| 4. NO-F | 5 mg/kg |

Eighteen hours after the last treatment the rats were sacrified to determine any gastrointestinal damage. No gross changes were observed in the gastroenteric tract of control animals.

In the animals treated with indomethacin ulceration was observed in the stomachs and, additionally, the intestines of most animals (7/19) and in some cases (3/10) even diffuse adherences. In the group treated with NO-I, only gastric ulcers were observed in 1 animal, and in the group treated with NO-F one animal with a gastric ulcer and an animal with a duodenal ulcer were found.

Examples 18-18A and 18-B (Comparison)

Studies of Nitroxysynthetase Activity

The nitroxy-sinthetase inhibiting activity induced by lipopolisaccharide (LPS) was determined in rat neutrofils after administration of any of the test compounds and compared with that obtained after treatment with the suspending vehicle alone (0.5% carboxymethyl cellulose, 5 ml/kg) and a product used as comparison. Briefly, Wistar rats fasted for 24 hours before treatment received one of the test compounds (10 mg/kg) intraperitoneally or the vehicle LPS (5 mg/kg) intravenously (caudal vein).

Four hours later the animals were sacrified. Blood was collected for neutrofil isolation.

The enzymatic activity was determined according to the od described by Assreuy J. et al. *Feedback inhibition of nitric oxide sinthase activity by nitric oxide*, British Journal of Pharmacology, 883-837, 1993.

As shown in Table 8, the test product was found to be very effective in inhibiting nitroxy sinthetase compared to the group treated with the vehicle alone and differently from the reference flufenamic.

TABLE 8

| EXAMPLE | COMPOUND | DOSE (mg/kg/i.p.) | NITROXY-SYNTHETASE ACTIVITY[a] |
|---|---|---|---|
| 18 A | Vehicle | — | 100 |
| 18 B | Flufenamic | 10 | 98 |
| 18 | NO-F | 10 | 63 |

[a] percentage compared to the group treated with the vehicle alone.

Conclusions From the Whole Tests

The derivatives of the invention were found to be active in several tests aimed at determining the potential pharmacological activity controlling urination.

It should also be noted that the derivatives of the invention were also found to be effective in a broader series of tests than that in which each reference drug was found to be active, confirming the hypothesis that these derivatives are endowed with a superior overall pharmacological activity in controlling urinary incontinence.

Furthermore, the derivatives of the invention were found to be better tolerated than the reference products. They appeared to be less harmful to the stomach than the corresponding anti-inflammatory agents and less hypotensive than the standard agents with vasorelaxing activity.

The combined characteristics mentioned above make the products of the invention superior to the reference agents.

What is claimed is:

1. A compound having the general formula:

$$A\text{-}X_1\text{—}NO_2$$

or a salt thereof, wherein:

A=RCO

R is selected from:

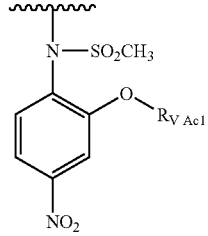

(V Ac1)

wherein $R_{VAc1}$ can be phenyl or cyclohexane,

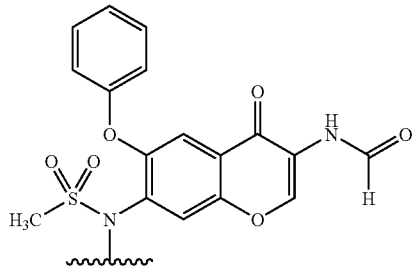

(V Ac2)

-continued

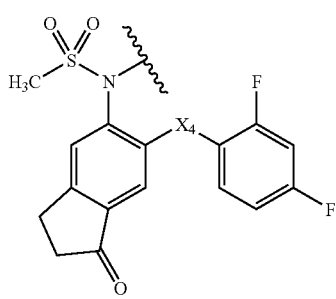

wherein X₄ can be sulfur or oxygen,

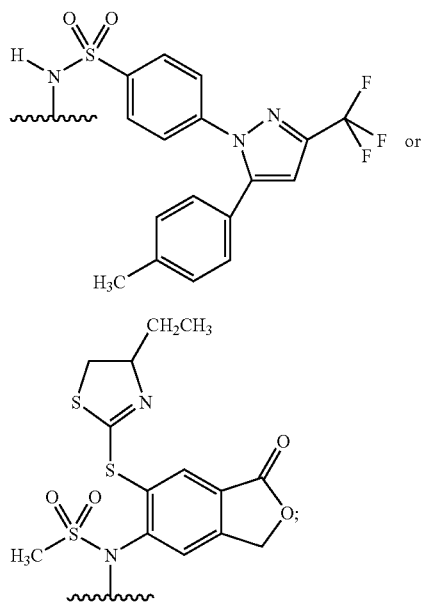

$X_1$ is a bivalent connecting bridge selected from:

YO, wherein

Y is linear or branched $C_2$ to $C_{20}$ alkylene, or an optionally substituted cycloalkylene having 5 to 7 carbon atoms, —(CH₂)ₙ₃—[phenyl]—CH₂—O—, wherein n3 is an integer from 0 to 3, HOOC—[phenyl(CH₂O—)(CH₂—)]—, —(CH₂—CH(ONO₂)—CH₂—O)ₙf'— wherein nf' is an integer from 1 to 6, or

—(CH(R₁f)—CH₂—O)ₙf—, wherein $R_{1f}$=H, $CH_3$ and nf is an integer from 1 to 6.

2. The compound or a salt thereof according to claim 1, wherein Y is linear or branched $C_2$ to $C_5$ alkylene.

3. The compound or a salt thereof according to claim 1, wherein V Ac1 is N-[(2-phenoxy-4-nitro)phenyl]-N-(6-nitroxy)hexanoylmethane-sulphonamide.

4. A pharmaceutical composition comprising a pharmaceutically effective amount of the compound according to claim 2 and a pharmaceutically acceptable carrier.

* * * * *